US012023467B2

(12) United States Patent
Cabiri et al.

(10) Patent No.: US 12,023,467 B2
(45) Date of Patent: Jul. 2, 2024

(54) FILLING EXTENSION FOR A PHARMACEUTICAL SYRINGE CARTRIDGE (71) Applicant: West Pharma. Services IL, Ltd., Ra'anana (IL)

(72) Inventors: Oz Cabiri, Hod Hasharon (IL); Ran Hezkiahu, Herzliya (IL); Tal Hammer, Ramat-Gan (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 617 days.

(21) Appl. No.: 17/274,646

(22) PCT Filed: Sep. 11, 2019

(86) PCT No.: PCT/IL2019/051016
§ 371 (c)(1),
(2) Date: Mar. 9, 2021

(87) PCT Pub. No.: WO2020/053856
PCT Pub. Date: Mar. 19, 2020

(65) Prior Publication Data
US 2021/0252221 A1 Aug. 19, 2021

Related U.S. Application Data (60) Provisional application No. 62/729,657, filed on Sep. 11, 2018.

(51) Int. Cl.
*A61M 5/178* (2006.01)
*A61J 1/06* (2006.01)
(Continued)

(52) U.S. Cl.
CPC ............ *A61M 5/1782* (2013.01); *A61J 1/062* (2013.01); *B65B 3/003* (2013.01); *B65B 43/54* (2013.01)

(58) Field of Classification Search
CPC ....... A61M 5/1782; A61J 1/062; B65B 3/003; B65B 43/54
See application file for complete search history.

(56) References Cited

U.S. PATENT DOCUMENTS 5,479,969 A * 1/1996 Hardie .................... B65B 3/003
422/549
6,915,823 B2 * 7/2005 Osborne ............... B65B 7/2821
604/407

(Continued)

FOREIGN PATENT DOCUMENTS

| ES | 343744 | 9/1968 |
|----|--------|--------|
| JP | 2000102607 | 4/2000 |

(Continued)

OTHER PUBLICATIONS

Int'l Search Report and Written Opinion dated Jul. 1, 2020 in Int'l Application No. PCT/IL2019/051016.

Primary Examiner — Andrew M Tecco
Assistant Examiner — Nicholas E Igbokwe
(74) Attorney, Agent, or Firm — Blank Rome LLP (57) ABSTRACT An extender for filling a syringe cartridge at a filling station having an elevating bar has a connector portion connecting a proximal portion of the extender to a distal portion of the syringe cartridge. A head on a distal portion of the extender is sized and shaped to engage the elevating bar of the filling station. The syringe cartridge having the extender may be provided to a filling station that is configured for filling a long syringe cartridge having a long syringe-cartridge length greater than a length of the syringe cartridge. The syringe cartridge and extender may be supported on a syringe support of the filling station and passed through the filling station to fill the syringe cartridge.

16 Claims, 6 Drawing Sheets (51) Int. Cl.
*A61M 1/06* (2006.01)
*B65B 3/00* (2006.01)
*B65B 43/54* (2006.01)

(56) References Cited

U.S. PATENT DOCUMENTS

| | | | |
|---|---|---|---|
| 7,232,038 | B2 | 6/2007 | Whitney |
| 7,270,158 | B2 * | 9/2007 | Py .............................. B65B 7/00 |
| | | | 141/130 |
| 2004/0159364 | A1 * | 8/2004 | Landau ................... B65B 3/003 |
| | | | 141/2 |
| 2011/0315269 | A1 | 12/2011 | Williamson et al. |
| 2017/0305580 | A1 * | 10/2017 | Heath ...................... B65B 3/003 |
| 2018/0071454 | A1 * | 3/2018 | Betts .......................... A61J 1/12 |
| 2018/0126066 | A1 * | 5/2018 | Narvekar ................. A61J 1/062 |
| 2020/0046899 | A1 * | 2/2020 | Cane' .................. A61M 5/2053 |

FOREIGN PATENT DOCUMENTS

| | | |
|---|---|---|
| JP | 2008081135 | 4/2008 |
| JP | 2018064935 | 4/2018 |
| WO | 0152920 A2 | 7/2001 |
| WO | 2004073554 A2 | 9/2004 |
| WO | 2018037398 | 3/2018 |

\* cited by examiner

FILLING EXTENSION FOR A PHARMACEUTICAL SYRINGE CARTRIDGE

CROSS-REFERENCE TO RELATED APPLICATIONS

This application is a section 371 of International Application PCT/IL19/51016, filed Sep. 11, 2019, which was published on Mar. 19, 2020 under Publication No. WO 2020/053856 A1, and which claims the benefit of U.S. Provisional Application 62/729,657 filed on Sep. 11, 2018. The entire contents of these applications are incorporated herein by reference in their entirety.

BACKGROUND OF THE INVENTION

The present invention relates to a filling extension for a pharmaceutical syringe cartridge. More specifically, the present invention relates to a filling extension for a pharmaceutical syringe cartridge allowing the pharmaceutical syringe cartridge to be filled by a pharmaceutical syringe cartridge filling station tooled to fill a pharmaceutical syringe cartridge having a different shape (e.g., longer or with a lateral extension) without requiring retooling of the filling station and/or without using new filling tray lifting mechanisms.

In commercial practice, multiple pharmaceutical syringe cartridges are simultaneously filled with a medicament at a filling station tooled to fill cartridges having a fixed configuration and size. Typically, the cartridges, supported by a flange, are placed in a nesting tray which is passed through a filling station that deposits a medicament in each of the cartridges in the tray. Thereafter, the cartridges are engaged by a lift or support bar which removes the cartridges from the tray. To assure that the cartridges are simultaneously lifted from the nesting tray by the lift bar, the cartridges must at least be of uniform length. Further, some syringe cartridges may not have a symmetric cross section, such as a distal end with an angled needle or needle cap.

U.S. Patent Application Publication No. 2017/0305580, hereafter referred to as the '580 Application, discloses a needle-free syringe and cap assembly and a filling tub system. A filling tub includes a plurality of sockets configured to receive and support a plurality of cap and syringe assemblies. Lifting bolt holes are provided for automated lifting mechanisms to extend through the floor of filling tub into contact with the cap to force the syringe and cap assembly from the socket. The '580 Application does not disclose a filling tub system able to simultaneously fill and discharge pharmaceutical syringe cartridges having differing configurations and/or lengths.

U.S. Pat. No. 7,232,038, hereafter referred to as the '038 Patent, discloses a disposable test tube rack comprising a first shell serving as a tray, a second shell serving as a cover, a central support panel and a lower support panel. Using both the central support panel and the lower support panel together provides support for taller test tubes. Using the lower support panel without the central support panel in place provides support for smaller test tubes. Although the '038 patent discloses a nesting tray that can accommodate test tubes of differing lengths, the nesting tray of the '038 patent has to be reconfigured to accommodate test tubes with a non-symmetric cross section.

Accordingly, there is a need in the art of pharmaceutical syringe cartridge filling to provide an extension allowing the simultaneous filling of pharmaceutical syringe cartridges of different configuration and size without the need to retool the filling station.

BRIEF SUMMARY OF THE INVENTION

Briefly stated, one embodiment of the present invention is directed to an extender for filling a syringe cartridge at a filling station having an elevating bar. The extender has a connector portion connecting a proximal portion of the extender to a distal portion of the syringe cartridge. A head on a distal portion of the extender is sized and shaped to engage the elevating bar of the filling station.

Another embodiment of the present invention is directed to a method of filling a syringe cartridge at a filling station comprising the following steps: providing a syringe cartridge having the extender, configuring the filling station for filling a long syringe cartridge having a long syringe-cartridge length greater than a length of the syringe cartridge; supporting the syringe cartridge and the extender on a syringe support of the filling station; and passing the syringe cartridge, the extender and the syringe support through the filling station to fill the syringe cartridge.

BRIEF DESCRIPTION OF THE SEVERAL VIEWS OF THE DRAWINGS

The foregoing summary, as well as the following detailed description of the various embodiments of the invention, will be better understood when read in conjunction with the appended drawings. It should be appreciated that the figures are not necessarily drawn to scale. The figures depict one or more implementations in accord with the present concepts, by way of example only, not by way of limitations. In the figures, like reference numerals refer to the same or similar elements.

In the drawings.

DETAILED DESCRIPTION OF THE INVENTION

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the cutter deck leveling fine adjustment, and designated parts thereof. The terminology includes the words noted above, derivatives thereof and words of similar import.

Although the words first, second, etc., are used herein to describe various elements, these elements should not be limited by these words. These words are only used to distinguish one element from another. For example, a first pharmaceutical syringe cartridge could be termed a second pharmaceutical syringe cartridge, and, similarly, a second pharmaceutical syringe cartridge could be termed a first pharmaceutical syringe cartridge, without departing from the scope of the present invention.

As used herein, the words "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The following description is directed towards various embodiments of a filling extension for a pharmaceutical syringe cartridge in accordance with the present invention.

Referring to the drawings in detail, where like numerals indicate like elements throughout, there is shown in FIGS. 1-6 a first preferred embodiment of the filling extension, generally designated 10 for a pharmaceutical syringe cartridge 100, and hereinafter referred to as the "extender" 10. The extender 10 may be attachable to a non-traditional, short pharmaceutical syringe cartridge 100 to facilitate the filling and/or handling of the short pharmaceutical syringe cartridges 100 by cartridge filling stations 200 designed for longer syringe cartridges. The filling station 200 may include nesting trays 210 removably disposable in filling tray tubs 212 to simultaneously fill a plurality of pharmaceutical syringe cartridges 100, 100L inserted in a plurality of apertures 214 in the nesting trays 210. (See, FIGS. 4 and 5)

Figure 1:
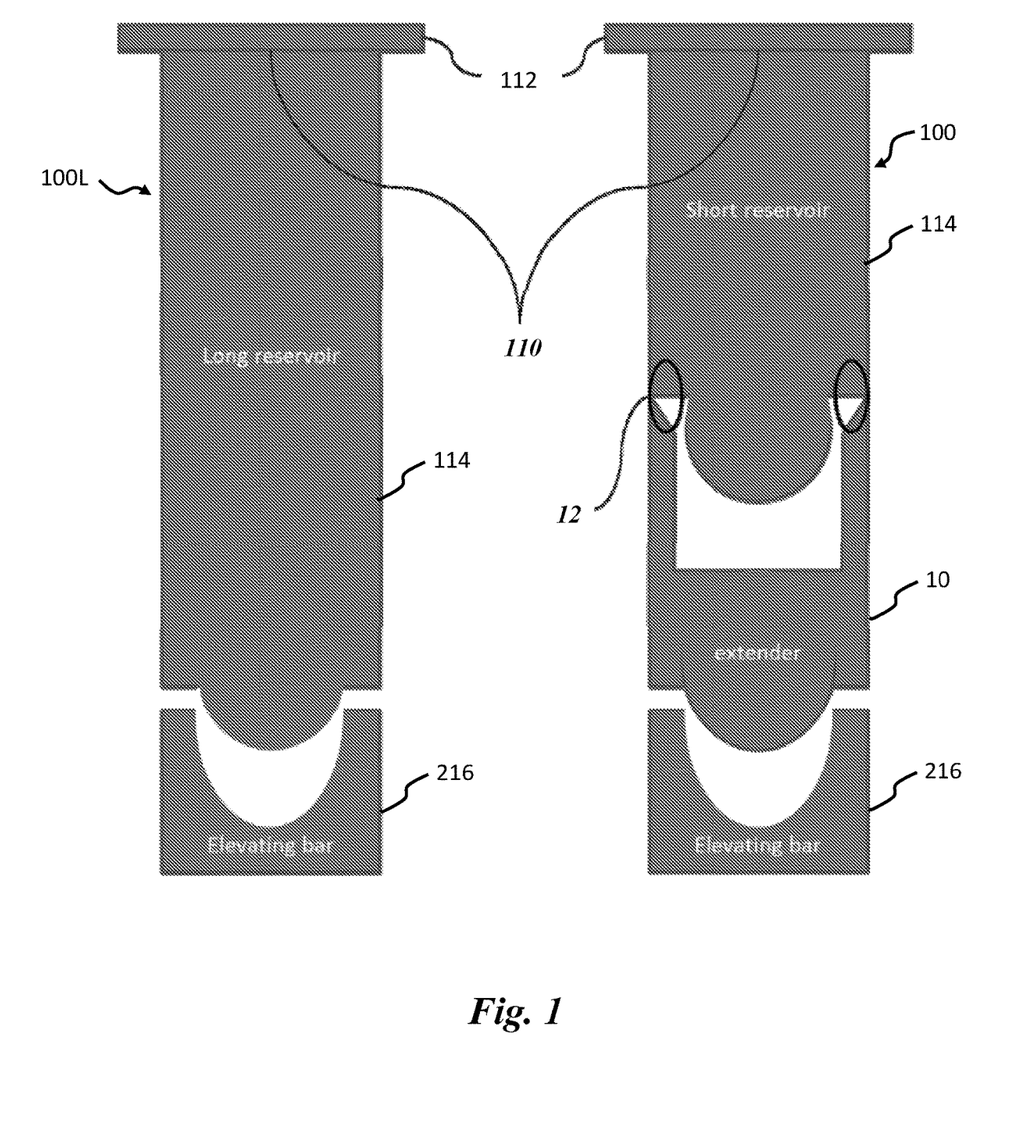
FIG. 1 is a schematic comparison of a long pharmaceutical syringe (left) with a short pharmaceutical syringe (right) with a filling extension in accordance with an embodiment of the present invention.

Referring to FIG. 1, a schematic comparison of a short syringe cartridge 100 with the extender 10 and a long pharmaceutical syringe cartridge 100L are shown. In some embodiments, the syringe cartridge 100 and the long syringe cartridge 100L may include a proximal opening 110 for receiving a medicament, a flange 112 surrounding the proximal opening 110 for supporting the cartridges 100, 100L in a filling tray 210, a reservoir 114 for retaining a medicament, and a distal fluid outlet 116 (for example, a cannula disposed in a removable cover). In some embodiments, the distal fluid outlet 116 may have a lateral extend 118 (see, FIG. 3) that is generally perpendicular to the longitudinal axis of the cartridge 100, 100L. For example, the lateral extend may include an angled needle and/or a needle cover.

The extender 10 includes a connector portion 12 on the proximal end of the extender 10. In some embodiments the connector portion 12 may be provided in the form of a bridge made of the same or similar material as the cartridge 100 and/or extender 10, such that the reservoir 114 and extender 10 are molded into a single unitary piece. In other embodiments, the connector portion 12 may be sized and shaped for attachment to the distal end of the short syringe cartridge 100 (e.g. threaded means, snap fit, friction fit, compression fit, etc.). In a preferred embodiment, the distal end of the short syringe cartridge 100 is provided with a beveled annular surface that mates with the connector 12. Alternatively, the connector portion 12 may rest on a non-beveled surface, for example, a dimple or recess 120 (see, FIG. 3) on the distal end of the reservoir 112. The extender 10 and/or cartridge 100 may include alignment features to preserve alignment or a relative orientation between the two components.

In some embodiments, the proximal end of the extender 10 may have one or more indentations 14 sized and shaped to fit around the lateral extend 118. At least a portion of the lateral extend 118 may extend through the one or more indentations 14 (see, FIGS. 3 and 4).

Figure 2:
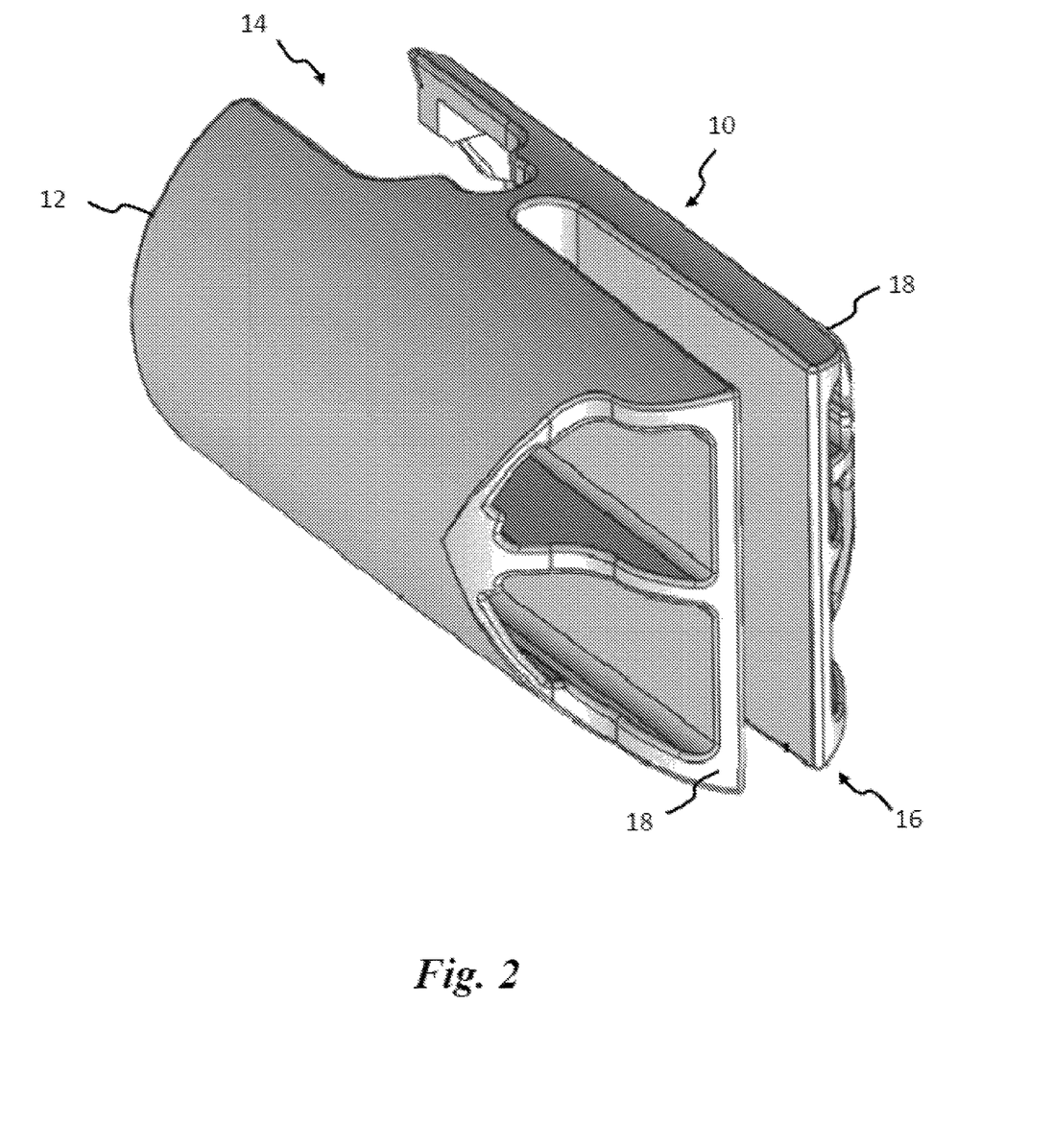
FIG. 2 is a perspective view of a filling extender in accordance with another embodiment of the present invention.
Figure 3:
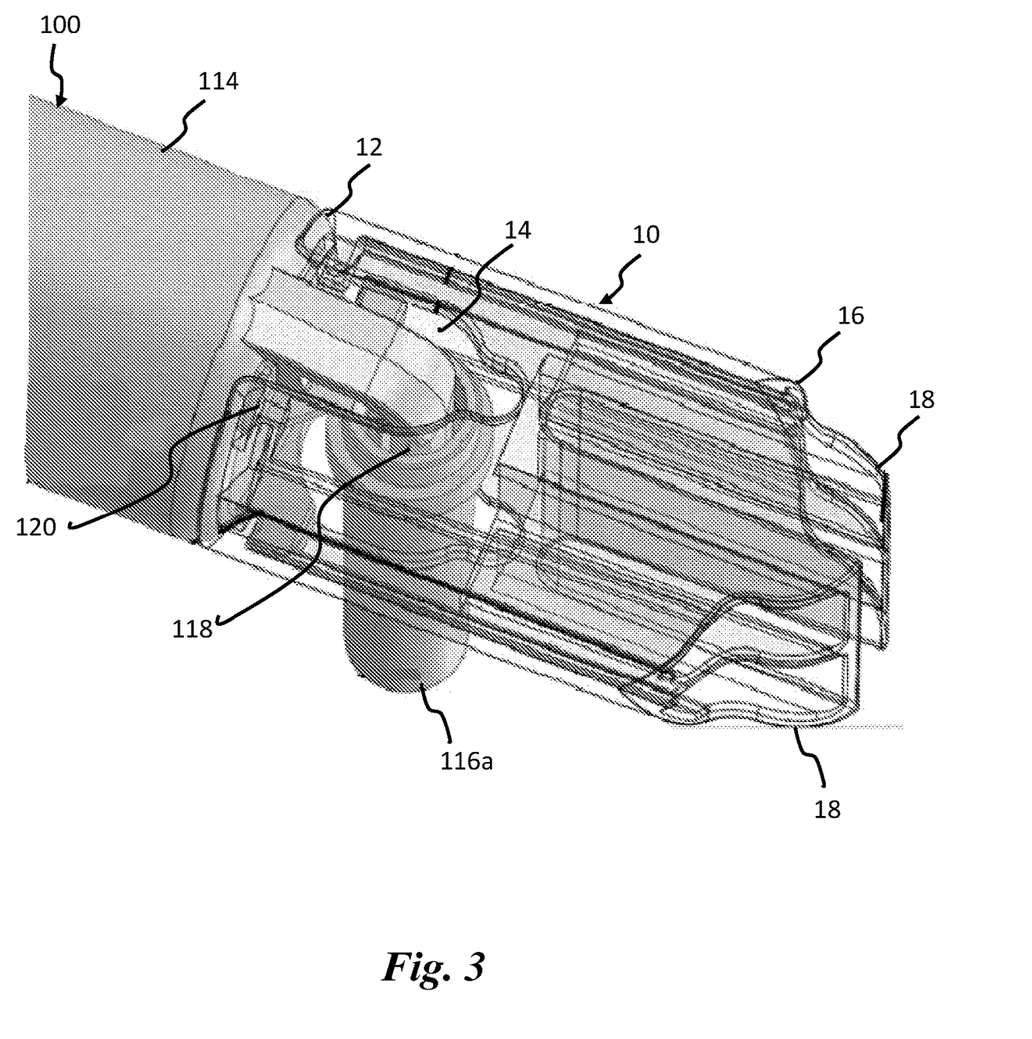
FIG. 3 is a perspective view partially in phantom lines of the filling extender of FIG. 2 connected to a distal end of a pharmaceutical syringe cartridge.
Figure 4:
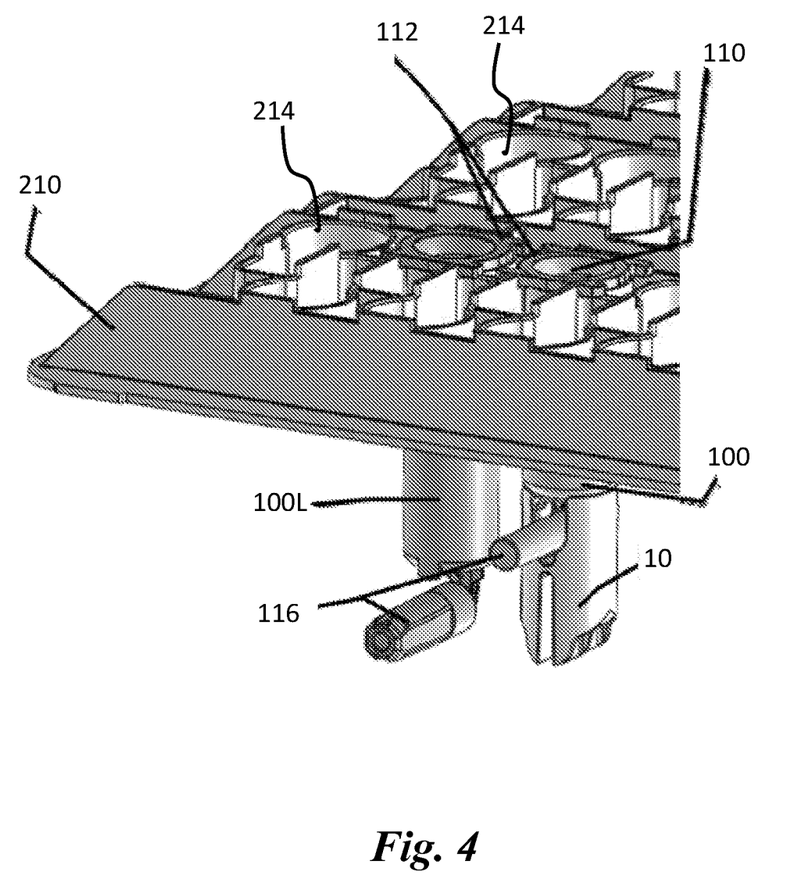
FIG. 4 is a perspective view of a short pharmaceutical syringe cartridge with the filling extension of FIG. 2 and a long pharmaceutical syringe cartridge supported by a filling tray in accordance with a preferred embodiment of the present invention.
Figure 5:
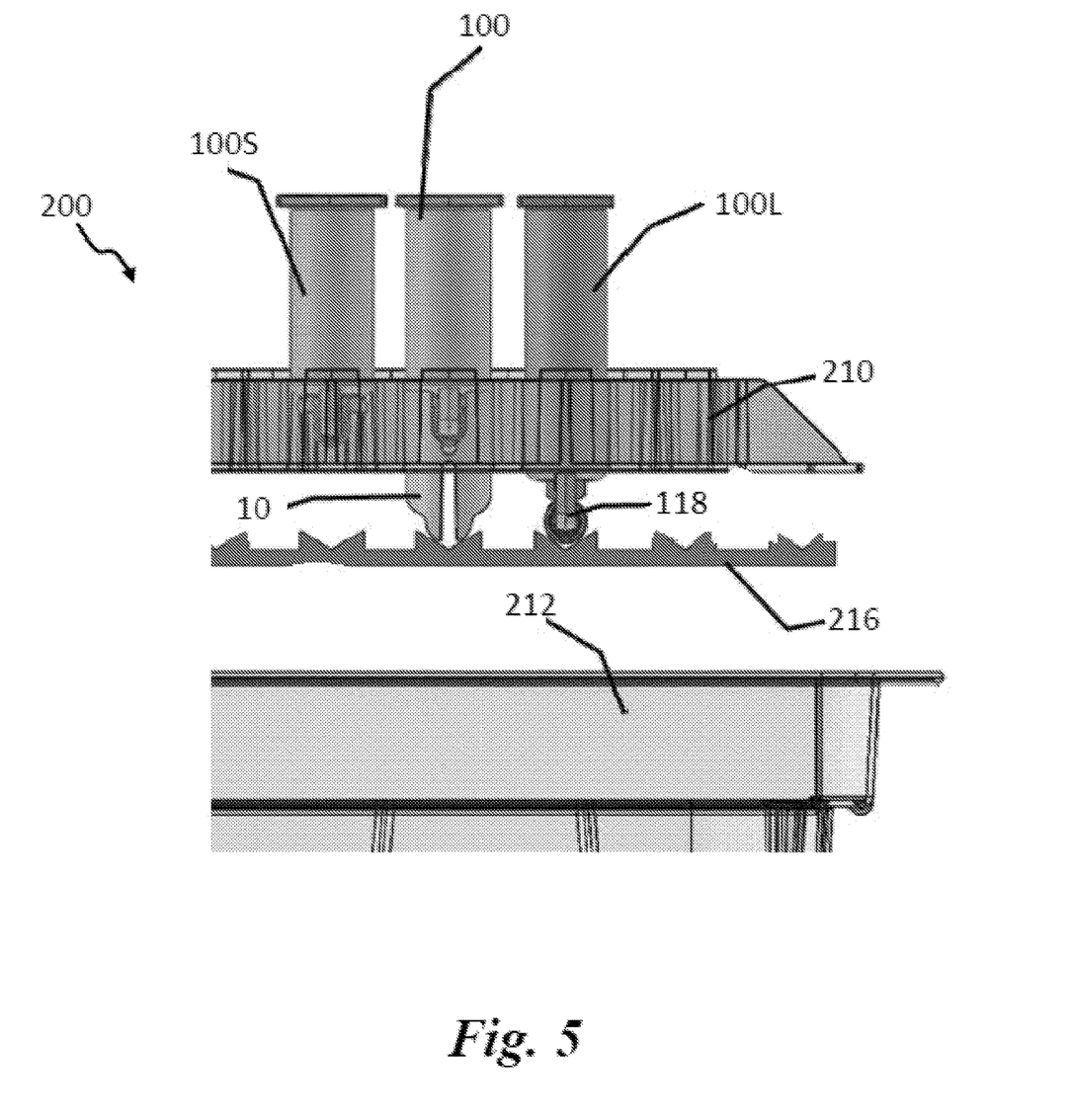
FIG. 5 is an orthogonal view illustrating (from left to right) a short pharmaceutical syringe cartridge without a filling extender, a short pharmaceutical syringe cartridge with the filling extender of FIG. 2, and a long pharmaceutical syringe cartridge raised by a lifting bar in a filling tray designed for the long cartridge in accordance with an embodiment of the present invention.

Referring to FIGS. 2 and 3, the extender 10 further includes a head 16 provided on the distal portion of the extender 10. The head 16 preferably has substantially the same or similar geometric configuration as the distal end of the long syringe cartridge 100L which is typically sized and shaped to fit a standard filling tray 210 and/or receive an elevating bar 216 of a filling station 200 as shown in FIGS. 4 and 5. In some embodiments, the head 16 may have spaced-apart prongs 18 for receiving therebetween the elevating bar 212 of the filling station 200 and in cooperation with the elevating bar 216 maintaining alignment of the syringe cartridges 100 and extenders 10 in the apertures 214 of the filling tray 210 during the filling process and the removal of the syringe cartridges 100 and extenders 10 thereafter. For example, as previously mentioned, a portion of a lateral extend 118 may extend through one or more indentations 14 of the extender 10. Therefore, the extender 10 and/or elevating bar 212 may include alignment features to maintain the orientation of the lateral extend 118 and allow the cartridge 100 to be lifted out of the filling tray 210 when the filling operation is complete.

When the extender 10 is attached to the reservoir 114 of the cartridge, the extender 10 gives the short syringe cartridge 100 a height or length which is substantially the same height or length as a long syringe cartridge 100L when positioned in a nesting tray, thereby avoiding the need for re-tooling the filling station 200 designed to accommodate long syringe cartridge 100L. Preferably, the length of the extender 10 is greater than 3 cm although the extender 10 according to various embodiments of the present invention may be more than 3 cm or less than 3 cm.

Referring again to FIGS. 4 and 5, the long syringe cartridge 100L and short syringe cartridge 100 may be suspended from the filling tray 210 by the previously described flange 112 located at a proximal end of the cartridges 100, 100L. In order to raise the cartridges 100, 100L for a filling operation, the elevating bar 216 engages either the lateral extend 118 of the long cartridge syringe 100L or the head 16 of the extender 10 for the short syringe cartridge 100.

Because a distal fluid outlet 116 of the long syringe cartridge 100L may be located within the lateral extend 118, contact between the elevating bar 216 and lateral extend 118 may compromise the sterility of the distal fluid outlet 116. For example, the contact surfaces of the elevating bar 216 may not be sterile. Alternatively, the force of the elevating bar 216 when it initially contacts the lateral extend 118 or the load of an elevated and filled long syringe cartridge 100L resting on the lateral extend 118 may inadvertently bend or break the lateral extend 118, once again compromising sterility. Therefore, it is an aspect of the invention to provide an extender 10 that is configured to remove or eliminate any contact between the elevating bar 216 and the lateral extend 116 of the short syringe cartridge 100. It is another aspect of the invention to provide an extender 10 that is configured to bear the load of a raised and filled short syringe cartridge 100 and reduce or eliminate any load on the lateral extend 116.

It is yet another aspect of the present invention to provide an extender that may reduce or eliminate the likelihood of the short syringe cartridges from tipping over before or during the filling operation. For example, referring again to FIG. 5, the short syringe cartridge 100S is illustrated at the elevation necessary to perform a filling operation. If an extender 10 is not included on the distal end of the short syringe cartridge 100S, the center of gravity of the short syringe cartridge 100S will be well above the top surface of the filling tray 210, thereby increasing the likelihood that the short syringe cartridge 100S will tip over either while it is being raised by the elevating bar 216 or during the filling operation.

Figure 6:
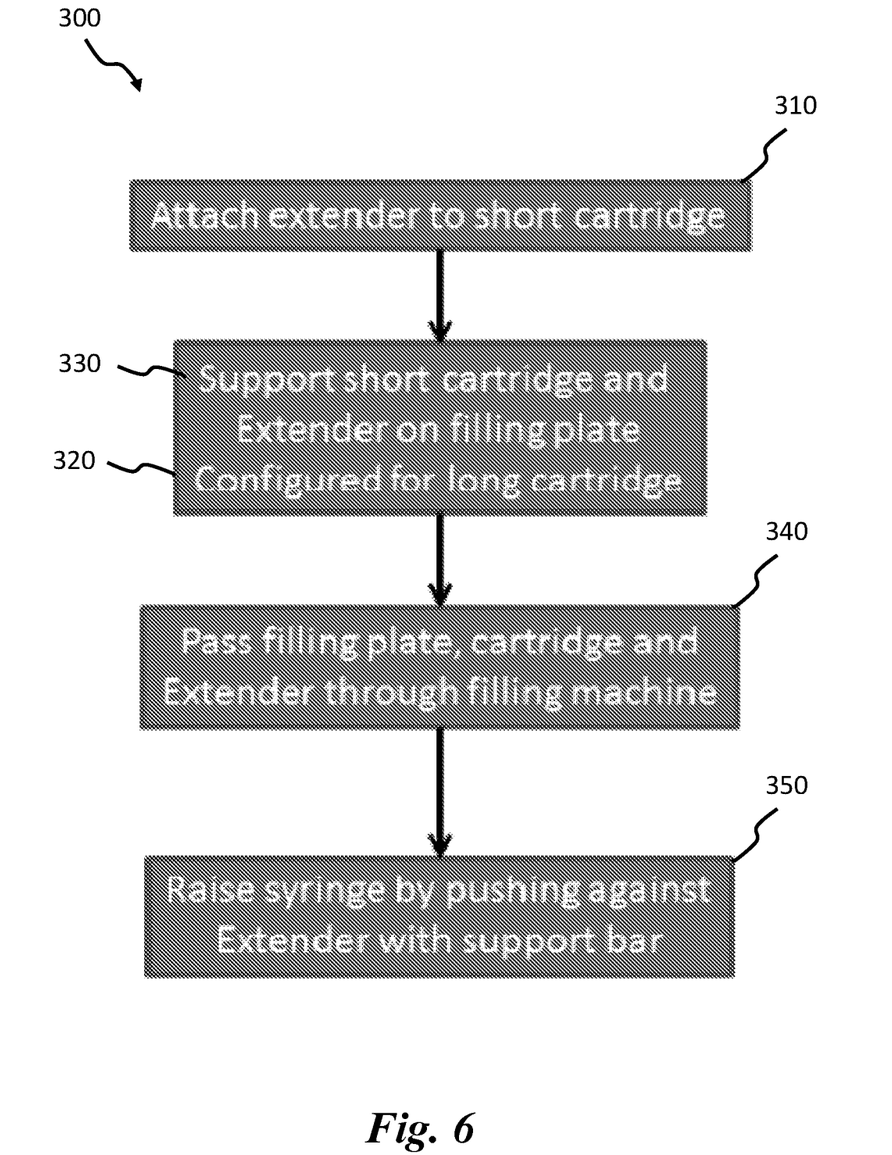
FIG. 6 is a is a flow chart of the steps of a method for using a filling extender according to yet another embodiment of the present invention.

FIG. 6 discloses a preferred method generally designated 300 for filling a syringe cartridge 100 in a filling station 200 using the extender 10 and is hereafter referred to as the "extender method" 300. The first step in the extender method 300 is providing a short syringe cartridge having an extender. In a preferred embodiment, the first step may comprise an attaching step 310 in which a removable extender 10 is first placed onto the distal end of a short syringe cartridge 100. The second step of the extender method 300 is a configuring step 320 in which the filling tray 210 of the filling station 200 is configured to receive and releasably retain long syringe cartridges 100L in the apertures 214. The third step in the extender method 300 is a supporting step 330 in which short syringe cartridges 100 with the extender 10 attached to the distal end thereof are supported in the apertures 214 of the filling tray 210 preferably by the flanges 112 at the proximal end of the syringe cartridges 100. The fourth step in the extender method 300 is a passing step 340 in which the filling tray 210 with the syringe cartridges 100 supported therein is passed through filing station 200. The fifth step of the extender method 300 is the raising step 350 in which the syringe cartridges 100 are raised in the filling tray 210 by the elevating bar 216 when the elevating bar 216 is pushed against the head 14 of the extender 10 of each syringe cartridge 100. Although the extender method 300 has been described above for a filling tray 210 only supporting short syringe cartridges 100, the method is equally applicable for any combination of short and long syringe cartridges 100, 100L in the filling tray.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

All references, patent applications, and patents mentioned above are incorporated herein by reference in their entirety and are not to be construed as an admission that any of the cited documents constitutes prior art, or as an admission against interest in any manner.

We claim:

1. An assembly comprising:
   a syringe cartridge having a longitudinal axis, the syringe cartridge comprising a distal fluid outlet; and
   an extender comprising:
   a sidewall defining an opening;
   a proximal portion comprising a connector that connects the proximal portion of the extender to a distal portion of the syringe cartridge; and
   a distal portion comprising a head,
   wherein the distal fluid outlet extends through the opening of the sidewall of the extender in the direction lateral to the longitudinal axis.

2. The assembly of claim 1, further comprising a cover, wherein:
   the syringe cartridge comprises a proximal opening and a reservoir,
   the cover covers the distal fluid outlet, and
   the connector is configured to connect to the reservoir.

3. The assembly of claim 2, wherein the opening in the sidewall of the extender comprises an indentation that extends from the proximal portion of the extender and that is configured to fit around the cover when the connector is connected to the reservoir.

4. The assembly of claim 1, wherein an axial length of the extender is greater than 3 cm.

5. The assembly of claim 1, wherein the connector of the extender and the distal portion of the syringe cartridge are unitary.

6. The assembly of claim 1, wherein the connector extends from a proximal portion of the extender and is configured to attach to a distal portion of the syringe cartridge.

7. The assembly of claim 1, wherein:
   the syringe cartridge is a second syringe cartridge, and
   the assembly is adapted for use with a filling station comprising an elevating bar, the filling station is adapted to accommodate a first syringe cartridge having a first height, and the elevating bar is configured to engage with a distal end of the first syringe cartridge.

8. The assembly of claim 7, wherein the second syringe cartridge has a second height that is less than the first height.

9. The assembly of claim 8, wherein the extender has an axial length equal to a difference between the first height and the second height.

10. The assembly of claim 9, wherein the head of the extender is configured, when the connector of the extender is connected to the distal portion of the second syringe cartridge, and when the second syringe cartridge is supported by the filling station, to engage with the elevating bar.

11. An assembly comprising:
    a first syringe cartridge having a first height;
    a second syringe cartridge having a second height less than the first height, the second syringe cartridge comprising a distal end comprising a geometric configuration, and an extender comprising:
- a proximal portion comprising a connector that connects the proximal portion of the extender to a distal portion of the second syringe cartridge; and
- a distal portion opposing the proximal portion and comprising a geometric configuration that is substantially the same as the geometric configuration of the distal end of the first syringe cartridge, wherein the extender has an axial length equal to a difference between the first height and the second height.

12. A method of filling a first syringe cartridge and a second syringe cartridge in a filling station, the first syringe cartridge having a first height and the second syringe cartridge having a second height that is less than the first height, the method comprising:

connecting a connector of a proximal portion of an extender to a distal portion of the second syringe cartridge, the extender having an axial length that is equal to a difference between the first height and the second height, and the extender comprising a distal portion opposing the proximal portion of the extender and comprising a geometric configuration that is substantially the same as a geometric configuration of a distal end of the first syringe cartridge;

supporting the first syringe cartridge and the second syringe cartridge on a syringe support of the filling station;

passing the first syringe cartridge and the second syringe cartridge through the filling station;

lifting the first syringe cartridge and the second syringe cartridge with an elevating bar of the filling station to engage the elevating bar with each of the distal end of the first syringe cartridge and the distal portion of the extender; and filling the first syringe cartridge and the second syringe cartridge.

13. The method of claim 12, wherein the syringe support includes a plurality of apertures therethrough arranged in an array, and the method further comprises:

passing a distal portion of the second syringe cartridge and the extender through an aperture of the plurality of apertures.

14. The method of claim 12 further comprising:

hanging the second syringe cartridge and the extender on the syringe support from a proximal portion of the second syringe cartridge.

15. The method of claim 12, wherein:

the second syringe cartridge includes a proximal opening, a reservoir, and a distal fluid outlet covered by a cover, and the extender is attached to the reservoir.

16. The method of claim 15, wherein the extender covers at least part of the cover.

* * * * *